United States Patent
Mease et al.

(10) Patent No.: US 6,201,022 B1
(45) Date of Patent: *Mar. 13, 2001

(54) METHODS FOR TREATING NEUROTRANSMITTER-MEDIATED PAIN SYNDROMES BY TOPICALLY ADMINISTERING AN OMEGA FATTY ACID

(75) Inventors: Philip J. Mease; Barry I. Bockow, both of Seattle; Marc D. Erlitz, Kirkland, all of WA (US)

(73) Assignee: MyoRx, Inc., Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/824,931

(22) Filed: Mar. 27, 1997

(51) Int. Cl.[7] .......................... A61K 31/20; A61K 31/60; A61K 31/61

(52) U.S. Cl. .......................... 514/560; 514/163; 514/165

(58) Field of Search .................................. 514/560, 163, 514/165

(56) References Cited

PUBLICATIONS

Kyle, Chemical Abstracts, vol. 122, abstract No. 123151., 1994.*
Cameron et al, Biological Abstracts, vol. 95, abstract No. 82368., 1994.*
Okuda et al, Chemical Abstracts, vol. 119, abstract No. 62803., 1993.*

* cited by examiner

*Primary Examiner*—William R. A. Jarvis
(74) *Attorney, Agent, or Firm*—Seed Intellectual Property Law Group PLLC

(57) ABSTRACT

Methods are disclosed for treating neurotransmitter-mediated pain syndromes such as fibromyalgia. Such methods include topically administering an effective amount of a composition containing an omega fatty acid in combination with a carrier or diluent. The composition may also contain a cyclo-oxygenase inhibitor and other optional components, such as vitamins A, E and/or C.

17 Claims, No Drawings

METHODS FOR TREATING NEUROTRANSMITTER-MEDIATED PAIN SYNDROMES BY TOPICALLY ADMINISTERING AN OMEGA FATTY ACID

TECHNICAL FIELD

This invention relates generally to methods for treating a neuritic pain syndrome by administration of a composition containing an omega fatty acid to a patient in need thereof.

BACKGROUND OF THE INVENTION

Pain is experienced in the body via nerve signaling (e.g., from a noxious stimulus to a peripheral nerve), which transmits an impulse via the nerve axon and neurochemical transmission to other nerves in a path up the spinal cord to the brain. There are a wide variety of potential noxious stimuli, including noxious alterations in pressure, temperature, nerve damage from external sources or internal disease and degeneration, inflammatory molecules, and so forth. For many conditions, exact diagnosis and treatment will lead to resolution of pain, or at least amelioration thereof. However, in many instances, the cause may not be ascertainable, and/or available treatment options may be ineffective or unacceptably harmful. Patients and physicians are then left to try analgesics. In these applications, such medicines are nonspecific, may be inadequate in effect, may be harmful, or have unwanted side effects.

Two major types of nervous system pathology include (1) disturbances of neurotransmitter function/modulation (hereinafter "neurotransmitter dysregulation syndromes"), and (2) diseases of the nerves themselves (hereinafter "neuropathies"). A representative neurotransmitter dysregulation syndrome includes fibromyalgia (FM), and representative neuropathies include diabetic and alcoholic neuropathies, as well as complications resulting from use of certain indications and aging. FM is a common condition characterized by a history of chronic generalized pain and physical exam evidence of at least 11 of 18 defined "tender point" sites in muscles and connective tissue (Wolfe et al., *Arthritis Rheum* 33:160–72, 1990). Commonly associated conditions include irritable bowel syndrome, headache, irritable bladder syndrome (interstitial cystitis), sleep disturbance, and fatigue (Goldenberg, *Current Opinion in Rheumatology* 8:113–123, 1996; Moldofsky et al., *Psychosom Med* 37:341–51, 1975; Wolfe et al., 1990; Wolfe et al., *J Rheum* 23:3, 1996; Yunus et al., *Semin Arthritis Rheum* 11:151–71, 1981). The prevalence in the general population is approximately 2% and occurs predominantly in females (Goldenberg, 1996; Wolfe, *Arthitis Rheum* 38:19–28, 1995; Wolfe et al., 1996).

A predominant theory regarding the etiology of FM holds that an imbalance and/or dysregulation of neurotransmitter function may occur within the central nervous system (CNS), either in the brain or spinal cord and in the relation of the CNS to muscle and connective tissue via regulatory nerve pathways (Goldenberg, 1996; Russell, *Rheum Dis Clin NA* 15:149–167, 1989; Russell et al., *J Rheumatol* 19:104–9, 1992; Vaeroy et al., *Pain* 32:21–6, 1988; Wolfe et al., 1996). Neurotransmitters are chemical messengers, neuropeptides, emitted from nerve cells that interact with receptors on other nerve cells, as well as other cell types, including muscle and immune cells. Neurotransmitter imbalance, which leads to increased pain experience, may include a qualitative and/or quantitative decrease in the function of such neurotransmitters as serotonin, norepinephrine, dopamine, endorphins, and encephalins and an increase in the irritative neurotransmitter, substance P. This imbalance results in amplified modulation of pain-signaling in the central nervous system, resulting in neurogenic pain (Matucci-Cerinic, *Rheumatic Disease Clinics of North America* 19:975–991, 1993; Bonica, *The Management of pain*, Lea and Febiger, 2d ed., Philadelphia, pp. 95–121, 1990). Similar mechanisms may be at work to cause associated conditions; for example, dysregulation of neurotransmitter signaling in the bowel musculature, leading to irritable bowel syndrome symptoms such as cramping, diarrhea, and/or constipation.

At the current time, treatment options for FM are generally not optimally effective. Low doses of antidepressant medications may improve neurotransmitter dysregulation, leading to partial and temporary improvement in pain (Goldenberg et al., *Arthritis Rheum* 29:1371–7, 1986; Simms, *Ballieres Clin Rheumatol* 8:917–934, 1994; Wolfe et al., 1996). Analgesics, muscle relaxants, and nonsteroidal anti-inflammatory drugs may have a mild beneficial effect on pain (Simms; Wolfe et al., 1996). Physical modalities such as physical therapy, stretching, and exercise can partially help, as can acupuncture (Burckhardt et al., *Scan J Rheumatol* 94:51, 1992; Simms; Wolfe et al., 1996). Stress reduction techniques and psychological counseling may allow the patient to accommodate to the symptoms (Burckhardt et al.; Simms; Wolfe et al., 1996). FM is usually a chronic condition and can be as disabling as rheumatoid arthritis (Griep; Hawley et al., *J Rheumatol* 18:1552–7, 1991; Martinez et al., *J Rheumatol* 22:270–274, 1995; Mason et al., *Arthritis Rheum* (suppl) 32:5197, 1989; Wolfe et al., *J Rheum* 23:3, 1996). Clearly, additional and more effective treatments are needed to reduce suffering from this condition.

Whereas FM exemplifies a neurotransmitter dysregulation syndrome, there are numerous conditions characterized by ultrastructural change of the nerves themselves, as mentioned above, called neuropathies (Adams, *Principles of Neurology*, Victor M. (eds.), 4th ed., 1989, McGraw Hill, New York; Bonica).

Diseases of the sensory nerves, as well as sympathetic and parasympathetic nerves of the peripheral nervous system, can yield pain and other unpleasant sensations called paresthesia or dysesthesia. These can be classified according to where pathology occurs, e.g., the anterior or lateral horns of the spinal cord, the dorsal root or sympathetic ganglia, as well as whether the nerve (axon) itself or myelin sheath is affected. Pathologic processes can include aging, infection, ischemia, immunologic inflammation, direct toxic effects, and other insults. Examples of painful neuropathies, especially effecting the extremities, include those associated with diabetes, alcoholism, shingles, side effects of various medications, cancers, autoimmune diseases, sympathetic dystrophies, and aging. In many cases, no specific etiology is found. These conditions are unfortunately common and treatment approaches are only minimally helpful. Examples of treatments include analgesic, anti-depressant, and anti seizure medications. Unfortunately, these tend to be only partially helpful and may have harmful side effects.

Accordingly, there is a need in the art for compositions and methods for treating pain generally associated with disturbances of the nervous system, including diseases of the central and peripheral nervous system, as well as pain induced by neuropeptide dysfunction. Such methods should also avoid the disadvantages typically associated with oral or systemic delivery of pain medications. The present invention fulfills these needs and provides other related advantages.

SUMMARY OF THE INVENTION

In brief, the present invention is directed to the treatment of neuritic pain syndromes. As used herein, "neuritic pain syndromes" include pain syndromes associated with a disease or abnormality of the nervous system (i.e., "neuropathy"), including neurotransmitter-mediated pain syndromes. Furthermore, the term "treatment" means a reduction or alleviation of pain associated with a neuritic pain syndrome. Thus, a decrease in pain constitutes treatment in the context of this invention.

Methods of this invention involve the topical administration of a composition to a patient in need thereof, and preferably topical administration on or in close proximity to the tissue associated with the pain. Compositions of this invention include one or more omega fatty acids, such as omega-3 and omega-6 fatty acids, in combination with an acceptable topical carrier or diluent. The composition may optionally contain additional components, such as a cyclooxygenase inhibitor, as disclosed in greater detail below.

These and other aspects of this invention will become evident upon reference to the following detailed description. To this end, references are set forth herein for the purpose of supplementing certain aspects of this invention. Such references are hereby incorporated by reference in their entirety.

DETAILED DESCRIPTION OF THE INVENTION

As mentioned above, the present invention is generally directed to methods for treating neuritic pain syndromes by topical administration of a composition of this invention to a warm-blooded animal in need thereof (also referred to herein as a "patient"). Such compositions include one or more omega fatty acids in combination with an acceptable carrier or diluent, and are formulated for topical administration to the patient.

Fatty acids are a class of organic compounds that are characterized by a long hydrocarbon chain terminating with a carboxylic acid group. Fatty acids have a carboxyl end and a methyl (i.e., "omega") end. Omega-3 fatty acids are derived from marine sources, while omega-6 fatty acids are derived from botanical sources. In addition to the difference in their origins, these omega fatty acids may be distinguished based on their structural characteristics.

Omega-3 fatty acids are a family of polyunsaturated fatty acids where the unsaturated carbon most distant from the carboxyl group is the third carbon from the methyl terminus. Omega-3 fatty acids have the following general formula:

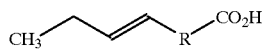

where R is a saturated or unsaturated, substituted or unsubstituted, branched or straight chain alkyl group having from 1 to 20 carbon atoms. Preferably, R is an unsaturated straight chain alkyl having from 13 to 17 carbon atoms (i.e., an omega-3 fatty acid having from 18 to 22 total carbon atoms), and containing from 2 to 6 carbon-carbon double bonds. In a preferred embodiment, the compositions of the present invention comprise omega-3 fatty acids which contain 20 carbon atoms with 5 carbon-carbon double bonds, or 22 carbon atoms with 6 carbon-carbon double bonds, including (but not limited to) eicosapentaenoic acid ("EPA") and docosahexaenoic acid ("DHA"):

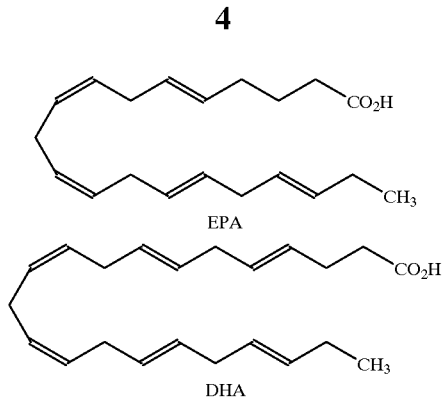

Similarly, omega-6 fatty acids are a family of unsaturated fatty acids where the unsaturated carbon most distant from the carboxyl group is the sixth carbon from the methyl terminus. Omega-6 fatty acids have the following general formula:

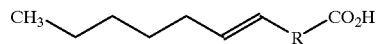

where R is a saturated or unsaturated, substituted or unsubstituted, branched or straight chain alkyl group having from 1 to 20 carbon atoms. Preferably, R is an unsaturated straight chain alkyl having from 10 to 14 carbon atoms (i.e., an omega-6 fatty acid having from 18 to 22 total carbon atoms), and containing from 2 to 6 carbon-carbon double bonds. In a preferred embodiment, the compositions of the present invention comprise omega-6 fatty acids which contain 18 carbon atoms with 3 carbon-carbon double bonds, or 20 carbon atoms with 4 carbon-carbon double bonds, including (but not limited to) gamma-linolenic acid ("GLA") and dihomo-gamma-linolenic acid ("DHGLA"):

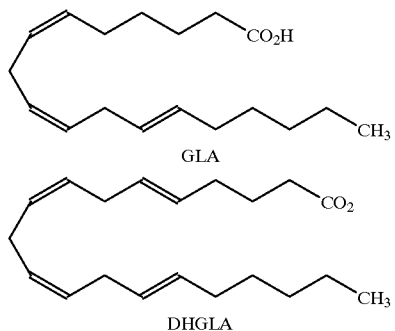

The omega fatty acid of the present invention may comprise an omega-3 fatty acid, an omega-6 fatty acid, a mixture of two or more omega-3 fatty acids, a mixture of two or more omega-6 fatty acids, or a mixture of one or more omega-3 and one or more omega-6 fatty acids.

For purposes of administration, the compositions of the present invention are formulated in any suitable manner for topical application to a surface (such as the skin or mucosal tissue) of the patient's body which is to be treated. Such formulations contain effective amounts of an omega fatty acid, as well as one or more pharmaceutically acceptable carriers or diluents. More specifically, the formulations of the present invention may be administrated in the form of liquids containing acceptable diluents such as deionized water and alcohol, or may be administered as suspensions, emulsions, gels or creams containing acceptable diluents or carriers to impart the desired texture, consistency, viscosity and appearance. Such acceptable diluents and carriers are familiar to those skilled in the art and include (but are not limited to) fatty alcohols, fatty acids, fatty esters, organic and inorganic bases, steroid esters, triglyceride esters, phospholipids such as lecithin and cephalin, polyhydric alcohol esters, hydrophobic lanolin derivatives, hydrocarbon oils, cocoa butter waxes, silicon oils, preserving agents, pH balancers and cellulose derivatives. One skilled in the art may further formulate the components of this invention in an appropriate manner, and in accordance with accepted practices, such as those disclosed in *Remington's Pharmaceutical Sciences*, Gennaro, Ed., Mack Publishing Co., Easton, Pa. 1990.

The omega fatty acid is present in the composition in an amount sufficient to treat a neuritic pain syndrome when administered topically to the patient. When formulated for such administration, the omega fatty acids may be present in an amount ranging from 1% to 65% by weight (based on the total weight of the formulation), more preferably from 2% to 40% by weight, and most preferably from 3% to 30%.

The composition may be applied daily in the form of, for example, a liquid, cream or gel directly to skin or mucosal tissue of the patient. For example, when formulated as a liquid, cream or gel, the composition may be applied generously to the desired area from 1 to 4 times daily and gently massage into the skin until fully absorbed. Following application, an occlusive dressing may be optionally applied for 4 to 10 hours to enhance efficacy. Absorption of the composition can be further enhanced by phoresis, ultrasound and other physical therapy modalities.

In addition to one or more omega fatty acids and an acceptable carrier or diluent, the compositions of the present invention may optionally contain a cyclooxygenase inhibitor. Cyclooxygenase inhibitors of the present invention include any compound which effectively inhibits cyclooxygenase, including (but not limited to) acetylating and non-acetylating inhibitors. Cyclooxygenase inhibitors which acetylate cyclooxygenase (i.e., "acetylating inhibitors") include acetylsalicylic acid (aspirin) and methyl salicylic acid, as well as salts thereof. Cyclooxygenase inhibitors which do not acetylate cyclooxygenase (i.e., "non-acetylating inhibitors") include (but are not limited to) salicylates such as salicylic acid, salicylsalicylic acid, trilisate, and disalcid, and salts thereof. Other cyclooxygenase inhibitors include naproxen, piroxicam, indomethacin, sulindac, meclofenamate, diflunisal, tolmetin, etodolac, ketorolac, diclofenac, ibuprofen, fenoprofen, ketoprofen and nabumetome. When present in the composition, a cyclooxygenase inhibitor is included in an amount sufficient to treat the neuritic pain syndrome when topically administered to the patient in combination with the omega fatty acid.

The compositions of the present invention may also contain further optional components including, but not limited to, vitamin A, vitamin E, vitamin C, Carbomer 2001 (a carboxyvinyl polymer thickening agent), squalene, aloe vera, and capsaicin.

When present, the cyclooxygenase inhibitor is present in an amount ranging from 3% to 25% by weight, vitamin A, C and/or E each optionally present in an amount ranging from 0.5% to 3% by weight, squalene optionally present in an amount ranging from 5% to 20% by weight, Carbomer 2001 (e.g., 2% solution) optionally present in an amount ranging from 5% to 15% by weight, aloe vera optionally present in an amount ranging from 0.2% to 5% by weight, and capsaicin optionally present in an amount ranging from 0.1% to 1% by weight. Example 1 further illustrates representative formulations of the compositions of the present invention for topical application.

The methods of the present invention provide a unique approach to the treatment of neuritic pain syndromes including neurotransmitter-dysregulation pain syndromes and neuropathies. Neurotransmitter-dysregulation pain syndromes generally involve normal nerves, but possess subtle alterations in quantity and quality of the various neurotransmitter molecules like serotonin, norepinephrine, and substance P which are released by the sending terminal of one neuron and interact with receptors on the receiving terminal of another neuron. These subtle alterations lead to modulation of a nerve signal such that it is interpreted as pain or as more painful.

More specifically, sensory neuropeptides are released from the afferent nerve ending of one nerve cell and received by receptors at the afferent end of another nerve cell. They are chemical messengers which transmit signal. There are numerous neuropeptides, including serotonin, dopamine, norepinephrine, somatostatin, substance P, and calcitonin gene-related peptide. Alterations in the quantity of neuropeptide release, changes in the afferent receptor, changes of re-uptake of the neuropeptides can all yield qualitative change of the neural signaling process, including an increase or decrease of pain modulation. FM is characterized by a relative deficit of serotonin effect and relative excess of substance P effect. Most pain states, including at a nerve receptor level in some of the peripheral neuropathies, and many "idiopathic" chronic pain conditions, have neuropeptide dysregulation as a feature of the nociceptive state. Other examples include reflex sympathetic dystrophy and myofascial pain syndrome. Although not intending to be bound by the following theory, it is believed that the compositions of this invention enter the cell membrane and lead to up-regulation of serotonin release or reception and possibly down-regulation of its re-uptake (to increase time in the nerve synapse), and/or down-regulation of substance P release or reception. Similar effects are believed to occur with regard to other neuropeptides, i.e., upping effect of the pain-relieving ones and downing the effect of the noxious ones.

In contrast to neurotransmitter-dysregulation pain syndromes, neuropathies generally involve abnormalities in the nerve itself, such as degeneration of the axon or sheath. This derangement of nerve cell is experienced as pain. For example, there are neuropathies in which the cells of the myelin sheath, the Schwann cells, may be dysfunctional, degenerative, and/or may die off, while the axon remains unaffected. Alternatively, there are neuropathies where just the axon is disturbed, as well as combinations of both conditions. Neuropathies may also be distinguished by the process by which they occur and their location (e.g. arising in the spinal cord and extending outward or vice versa). Diphtheria polyneuropathy is an example of a myelin sheath disorder-although an infectious disease, there is no evidence of inflammatory cell infiltration. Arsenic poisoning neuropathy is an example of a more pure axonal neuropathy. Diabetes induces a mixed myelin-axonal neuropathy.

Although not intending to be bound by the following theory, it is believed that one mechanism whereby pain is experienced is aberrant discharges arising in diseased nociceptive nerve fibers. Nociceptive refers to noxious sensation. Another mechanism is that loss of large touch-pressure nerves (non-noxious) leads to lack of inhibition of pain receiving nerve cells in the spinal cord. Thus, a composition of this invention enters the cell membrane of damaged nerve cells and, by altering the fatty acid composition, leads to a reduction of aberrant signaling by nociceptive fibers and/or alternatively improving signaling by non-noxious damaged nerve fibers. This leads to a restoration of a more normal balance of nerve signaling that results in neutralization of pain signaling.

Neuropathies treatable by the methods of this invention include: (I) syndromes of acute ascending motor paralysis with variable disturbance of sensory function, (II) syndromes of subacute sensorimotor paralysis, (III) syndromes of acquired forms of chronic sensorimotor polyneuropathy, (IV) syndromes of determined forms of chronic polyneuropathy, genetically, (V) syndromes of recurrent or relapsing polyneuropathy, and (VI) syndromes of mononeuropathy or multiple neuropathies (Adams and Victor, *Principles of Neurology*, 4th ed., McGraw-Hill Information Services Company, p. 1036, 1989). Representative syndromes within each of the above categories are listed in Table 1.

TABLE 1

Principal Neuropathic Syndromes

| Category | | Syndrome |
|---|---|---|
| I. | A. | Acute idiopathic polyneuritis (inflammatory polyradiculoneuropathy), Landry-Guillain-Barre syndrome (GBS), acute immune-mediated polyneuritis (AIMP) |
| | B. | Infectious mononucleosis and polyneuritis |
| | C. | Hepatitis and polyneuritis |
| | D. | Diphtheritic polyneuropathy |
| | E. | Porphyric polyneuropathy |
| | F. | Certain toxic polyneuropathies (triorthocresyl phosphate, thallium) |
| | G. | Acute axonal polyneuropathy |
| | H. | Rarely, paraneoplastic, vaccinogenic (smallpox, rabies), serogenic, polyarteritic, or lupus polyneuropathy |
| | I. | Acute panautonomic neuropathy |
| II. | A. | Symmetric polyneuropathies |
| | | 1. Deficiency states: alcoholism (beriberi), pellagra, vitamin $B_{12}$ deficiency, chronic gastrointestinal disease |
| | | 2. Poisoning with heavy metals and industrial solvents: arsenic, lead, mercury, thallium, methyl n-butyl ketone, n-hexane, methyl bromide, organo-phosphates (TOCP, etc.), acrylamide. |
| | | 3. Drug intoxications: isoniazid, ethionamide, hydralazine, nitrofurantoin and related nitrofurazones, disulfiram, carbon disulfide, vincristine, chloramphenicol, phenytoin, amitriptyline, dapsone, stilbamidine, trichlorethylene, thalidomide, Clioquinol, etc. |
| | | 4. Uremic polyneuropathy |
| | B. | Asymmetric neuropathies (mononeuropathy multiplex) |
| | | 1. Diabetes |
| | | 2. Polyarteritis nodosa and other inflammatory angiopathic neuropathies |
| | | 3. Subacute idiopathic polyneuropathies |
| | | 4. Sarcoidosis |
| | | 5. Ischemic neuropathy with peripheral vascular disease. |
| III. | A. | Carcinoma, myeloma, and other malignancies |
| | B. | Paraproteinemias |
| | C. | Uremia (occasionally subacute) |
| | D. | Beriberi (usually subacute) |
| | E. | Diabetes |
| | F. | Hypothyroidism |
| | F. | Hypothyroidism |
| | G. | Connective tissue diseases |
| | H. | Amyloidosis |
| | I. | Leprosy |
| | J. | Benign form in the elderly |
| | K. | Sepsis and chronic illness |

TABLE 1-continued

Principal Neuropathic Syndromes

| Category | | Syndrome |
|---|---|---|
| IV. | A. | Inherited polyneuropathies of predominantly sensory type |
| | | 1. Dominant mutilating sensory neuropathy in adults |
| | | 2. Recessive mutilating sensory neuropathy of childhood |
| | | 3. Congenital insensitivity to pain |
| | | 4. Other inherited sensory neuropathies, including those associated with spinocerebellar degenerations and Riley-Day syndrome and the universal anesthesia syndrome |
| | B. | Inherited polyneuropathies of mixed sensorimotor-autonomic types |
| | | 1. Idiopathic group |
| | | 2. Inherited polyneuropathies with a recognized metabolic disorder |
| V. | A. | Idiopathic polyneuritis (GBS) |
| | B. | Porphyria |
| | C. | Chronic inflammatory polyradiculoneuropathy |
| | D. | Certain forms of mononeuritis multiplex |
| | E. | Beriberi or intoxications |
| | F. | Refsum disease, Tangier disease |
| VI. | A. | Pressure palsies |
| | B. | Traumatic neuropathies (including irradiation and electrical injuries) |
| | C. | Idiopathic brachial and sciatic neuropathy |
| | D. | Serum and vaccinogenic (smallpox, rabies) neuropathy |
| | E. | Herpes zoster |
| | F. | Neoplastic infiltration of roots and nerves |
| | G. | Leprosy |
| | H. | Diphtheritic wound infections with local neuropathy |
| | I. | Migrant sensory neuropathy |

Neurotransmitter-dysregulation pain syndromes treatable by the methods of this invention include, in addition to the syndromes identified above, the syndromes listed in Table 2.

TABLE 2

Representative Neurotransmitter-Dysregulation Pain Syndromes

| A. | Relatively Generalized Syndromes |
|---|---|
| | 1. Stump pain |
| | 2. Causalgia |
| | 3. Reflex sympathetic dystrophy |
| | 4. Fibromyalgia or diffuse myofascial pain |
| | 5. Burns |
| B. | Relatively Localized Syndromes |
| | 1. Trigeminal neuralgia (tic douloureux) |
| | 2. Acute herpes zoster (trigeminal) |
| | 3. Panautonomic neuralgia (trigeminal) |
| | 4. Geniculate neuralgia (VIItn cranial nerve); Romsay Hunt syndrome |
| | 5. Glossopharyngeal neuralgia (IXth cranial nerve) |
| | 6. Neuralgia of the superior laryngeal nerve (vagus nerve neuralgia) |
| | 7. Occipital neuralgia |
| C. | Craniofascial Pain of Musculoskeletal Origin |
| | 1. Temporamandibular pain and dysfunction syndrome |
| D. | Suboccipital and Cervical Musculoskeletal Disorders |
| 1. | Myofascial syndrome cervical sprain or cervical hyperextension injury (whiplash) |
| 2. | Myofascial syndrome: sternocleidomastoid muscle |
| 3. | Myofascial syndrome: trapezius muscle |
| 4. | Stylohyoid process syndrome (Eagle's syndrome) |
| E. | Vascular Disease of the Limbs |
| | 1. Raynaud's disease |
| | 2. Raynaud's phenomenon |
| | 3. Frostbite and cold injury |
| | 4. Erythema pernio (chilblains) |
| | 5. Acrocyanosis |
| | 6. Livedo reticularis |
| F. | Pain in the Rectum, Perineum and External Genitalia |
| | 1. Neuralgia of iliohypogastric, ilioinguinal, or genitofemoral nerves |
| | 2. Testicular pain |

TABLE 2-continued

Representative Neurotransmitter-Dysregulation Pain Syndromes

G. Local Syndromes in the Leg or Foot-Pain of Neurological Origin
  1. Lateral femoral cutaneous neuropathy (neuralgia paresthetica)
  2. Obturator neuralgia
  3. Femoral neuralgia
  4. Sciatica neuralgia
  5. Interdigital neuralgia of the foot (Morton's metatarsalgia)
  6. Injection neuropathy
  7. Painful legs and moving toes The following examples are offered by way of illustration, not limitations.

EXAMPLES

Example 1

| Formulation A | |
| --- | --- |
| Gammalinolenic acid and/or Dihomogammalinolenic acid | 3–30% |
| Methyl Salicylate | 7–15 |
| Vitamin A | 1–3 |
| Vitamin E | 1–3 |
| Vitamin C | 1–3 |
| Water and other inert ingredients | 23–80 |
| Formulation B | |
| Gammalinolenic acid and/or Dihomogammalinolenic acid | 3–35% |
| Vitamin A | 1–3 |
| Vitamin E | 1–3 |
| Vitamin C | 1–3 |
| Water and other inert ingredients | 33–87 |
| Formulation C | |
| Gammalinolenic acid and/or Dihomogammalinolenic acid | 3–35% |
| Methyl Salicylate | 7–15 |
| Vitamin A | 1–3 |
| Vitamin E | 1–3 |
| Aloe Vera | 5–15 |
| Water and other inert ingredients | 21–81 |
| Formulation D | |
| Gammalinolenic acid and/or Dihomogammalinolenic acid | 3–30% |
| Methyl Salicylate | 7–15 |
| Vitamin A | 1–3 |
| Vitamin E | 1–3 |
| Vitamin C | 1–3 |
| Aloe Vera | 1–10 |
| Water and other inert ingredients | 28–84 |
| Formulation E | |
| Eicosapentaenoic Acid | 35–45% |
| Docosahexaenoic Acid | 5–10% |
| Salicylate | Less than 5% |
| Vitamin E | 2–5% |
| Other inert ingredients and preservatives | 18–51% |
| Water | 1–2% |
| Formulation F | |
| Eicosapentaenoic Acid | 45–58% |
| Docosahexaenoic Acid | 10–18% |
| Salicylate | Less than 5% |
| Vitamin E | 2–5% |
| Vitamin A | 1–3% |
| Other inert ingredients and preservatives | 2–37% |
| Water | 1–2% |
| Formulation G | |
| Gammalinolenic acid and/or Dihomogammalinolenic acid | 3–30% |
| Methyl Salicylate | 7–15 |
| Vitamin A | 1–3 |
| Vitamin E | 1–3 |
| Capascin C | 0.02–1.0 |
| Aloe Vera | 0–10 |
| Water and other inert ingredients | 23–80 |
| Formulation H | |
| Gammalinolenic acid and/or Dihomogammalinolenic acid | 3–30% |
| Piroxicam | 1–3 |
| Vitamin A | 1–3 |
| Vitamin E | 1–3 |
| Vitamin C | 1–3 |
| Water and other inert ingredients | 23–80 |

Example 2

A 37-year-old female is troubled with chronic insomnia, and becomes addicted to chronic sleep medications. Low doses of sedating antidepressants have been tried but have caused intolerable dry mouth and constipation. She develops a condition of generalized aching, with characteristic tender points of fibromyalgia. Insomnia is worsened because she frequently awakens due to pain. A cream as disclosed above in Example 1 is topically applied as a thin layer over painful muscle areas 2–3 times daily. Her pain diminishes to the point that it is barely noticeable, and her sleep pattern improves.

Example 3

A 59-year old bank executive presents with painful feet. Examination reveals heightened and unpleasant sensation in the feet. He curtails his usual physical activity because of the pain. After the physician gains his trust, h e admits to drinking three highballs per night and a glass of wine with lunch each day. This pattern has been present for at least ten years. The physician diagnoses alcoholic peripheral neuropathy. He is referred to an outpatient alcohol treatment program, which he successfully completes and returns to work. Application of a cream of Example 1, topically applied to his feet twice daily, leads to diminution of pain and he is able to regain normal function.

Example 4

A 22-year old female in graduate school develops a severe viral illness characterized by malaise, fever, cough, and generalized muscle aching. After two weeks of near prostration, she decides to take leave from school and returns to her home city. Medical work-up reveals a lethargic woman with generalized muscle pain. She has poor short term memory and concentration. Laboratory studies reveal modest elevation of liver enzymes and are otherwise normal. Over the next six months, symptoms improve somewhat, but she is left with a persistent fatigue, generalized muscle pain and continued subtle cognitive problems. She is treated with stimulating anti-depressants which help fatigue but cause her to be too jittery and to have difficulty with sleep. She cannot tolerate oral non-steroidal anti-inflammatory drugs because of stomach sensitivity. A cream of Example 1 is topically applied to painful areas and leads to significant diminishment of muscular pain, and is well tolerated. She attains improved sleep, feels less fatigue and has improved cognitive function. She gradually improves and the condition remits.

Example 5

A 45-year old metal worker goes hiking with his children near Lyme, Conn. At home, he discovers a tick has burrowed into his leg. Several days later, he develops a rash. His physician mistakenly considers this a contact dermatitis. Several months later, generalized arthritis begins. Blood tests are positive for Lyme disease. He is treated with aggressive antibiotic therapy. Arthritis symptoms improve. However, he develops generalized muscle pain and a rheumatologist recognizes this as "post-Lyme fibromyalgia." Treatment with low dose anti-depressants and oral anti-inflammatory drugs is ineffective. He is too drowsy with muscle relaxants. A topical cream of Example 1 is topically applied on painful areas. The muscle pain improves significantly and eventually remits.

Example 6

A 45-year-old female develops chronic neck pain after a horseback riding injury. Despite several months of treatment with physical therapy, anti-inflammatory medications and analgesics, her condition worsens and she develops generalized muscular aching, sleep disturbance, fatigue, abdominal pain, and urinary frequency. Laboratory studies are unremarkable. Physical exam reveals significant areas of tenderness with palpation of the sternum and lower back. She was previously high functioning as a lawyer in a busy legal practice. She is now only able to work half-time because of pain and fatigue. She develops gastric irritability with continued use of oral nonsteroidal anti-inflammatory medicines, and thus cannot use them anymore. Her physician is appropriately reluctant to prescribe habituating sleeping medication. She topically applies a cream of Example 1 to painful areas of the body. Within two weeks of steady application, she is noticing a significant and consistent decrease of pain generally. Her sleep improves as does fatigue. She is able to think more clearly and focus on her work, becoming more productive and able to work full time again. With continued application, she is not completely pain free, but the pain is significantly in the background and fatigue resolves. She is able to go for longer periods of time without the use of medication, using it on an as-needed basis. She has avoided side effects of oral medications.

Example 7

A 72-year-old male presents with a linear rash extending from his spine, around his rib cage, and to the anterior chest. It is intensely painful. His physician diagnoses "shingles" (herpes zoster). A cream of Example 1 is applied three times a day. Pain subsides. He avoids the complications of constipation and sedation from narcotic analgesics and there is no chronic pain from "post-herpetic neuralgia."

Example 8

A 65-year-old woman, a known insulin-dependent diabetic, presents with painful feet. She is unable to walk due to the severity of the pain. She is diagnosed with diabetic peripheral neuropathy. Amitriptyline is prescribed but causes constipation and unsteadiness on her feet. Narcotic analgesics make her sedated and constipated. A cream of Example 1 is topically administered and leads to 75% reduction in pain, when applied twice a day. She continues this treatment with no complications.

Example 9

A 32-year-old accountant sustains a leg fracture while skiing. While the fracture is healing, the foot and ankle of that extremity becomes swollen, red and painful. A three-phase bone scan suggests the diagnosis of reflex sympathetic dystrophy. All treatment modalities are ineffective. A cream of Example 1 is topically employed three times a day. Within two weeks, pain, swelling and redness are subsiding and he is able to function.

Example 10

A 48-year-old male goes on a climbing expedition in Nepal. He is caught in a blizzard at 27,000 feet and sustains severe frostbite of his hands. Chronic hand pain ensues. He applies a cream of Example 1 in a thin layer over his hands twice a day and pain diminishes.

Example 11

A 13-year-old boy awakens to find his bedroom consumed in flames. He is able to escape by opening the window and crawling down a downspout. However, his pajama pants catch on fire, leaving him with second and third degree burns on his calves. Even as the skin heals, he is left with persistent pain in these areas. He applies a cream of Example 1 in a thin layer over his calves twice a day, resulting in amelioration of the pain.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating a neurotransmitter-mediated pain syndrome associated with a disease or abnormality of the nervous system, comprising topically administering to a patient in need thereof an effective amount of a composition comprising an omega fatty acid in combination with an acceptable carrier or diluent.

2. The method of claim 1 wherein the neurotransmitter-mediated pain syndrome is selected from fibromyalgia, sympathetic dystrophy and myofascial pain syndrome.

3. The method of claim 1 wherein the neurotransmitter-mediated pain syndrome is fibromyalgia.

4. The method of claim 1 wherein the composition is topically administered in the form of a gel, cream or lotion.

5. The method of claim 1 wherein the composition is topically administered in the form of a cream.

6. The method of claim 1 wherein the omega fatty acid is an omega-6 fatty acid.

7. The method of claim 1 wherein the omega fatty acid is an omega-3 fatty acid.

8. The method of claim 1 wherein the omega fatty acid of the composition has at least one of the following structures:

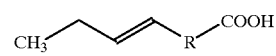

-continued

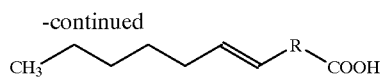

wherein R is a saturated or unsaturated, substituted or unsubstituted, branched or straight chain alkyl having from 1 to 20 carbon atoms.

9. The method of claim 1 wherein the omega fatty acid is eicosapentaenoic acid.

10. The method of claim 1 wherein the omega fatty acid is docosahexaenoic acid.

11. The method of claim 1 wherein the composition further comprises a cyclo-oxygenase inhibitor.

12. The method of claim 11 wherein the cyclo-oxygenase inhibitor is an acetylating inhibitor selected from acetylsalicylic acid, salicylsalicylic acid, and salts thereof.

13. The method of claim 11 wherein the cyclo-oxygenase inhibitor is a non-acetylating inhibitor selected from salicylic acid, trilisate, disalcid, and salts thereof.

14. The method of claim 11 wherein the cyclo-oxygenase inhibitor is selected from naproxen, piroxicam, indomethacin, sulindac, meclofenamate, diflunisal, tolmetin, ibuprofen, oxaprozin, etodolac, diclofenac, ketoprofen and nabumetone.

15. The method of claim 1 wherein the composition further comprises an ingredient selected from vitamin A, vitamin E, vitamin C, aloe vera, capsaicin, and mixtures thereof.

16. The method of claim 1 where the fatty acid is present in the composition in an amount ranging from 1 to 65% by weight.

17. The method of claim 1 where the fatty acid is present in the composition in an amount ranging from 2 to 40% by weight.

* * * * *